(12) United States Patent
Herrmann

(10) Patent No.: US 11,110,268 B1
(45) Date of Patent: Sep. 7, 2021

(54) DEVICE FOR TRANSCRANIAL BRAIN STIMULATION

(71) Applicant: Carl von Ossietzky Universität Oldenburg, Oldenburg (DE)

(72) Inventor: Christoph Herrmann, Oldenburg (DE)

(73) Assignee: CARL VON OSSIETZKY UNIVERSITÄT OLDENBURG

(*) Notice: Subject to any disclaimer, the term of this patent is extended or adjusted under 35 U.S.C. 154(b) by 405 days.

(21) Appl. No.: 16/341,293

(22) PCT Filed: Sep. 18, 2017

(86) PCT No.: PCT/EP2017/073393
§ 371 (c)(1),
(2) Date: Apr. 11, 2019

(87) PCT Pub. No.: WO2018/082839
PCT Pub. Date: May 11, 2018

(30) Foreign Application Priority Data

Nov. 2, 2016 (DE) .................... 10 2016 221 478.0

(51) Int. Cl.
*A61N 1/04* (2006.01)
*A61N 1/36* (2006.01)
(52) U.S. Cl.
CPC ....... *A61N 1/0456* (2013.01); *A61N 1/36025* (2013.01)
(58) Field of Classification Search
CPC .......................... A61N 1/0456; A61N 1/36025
See application file for complete search history.

(56) References Cited

U.S. PATENT DOCUMENTS

| 4,858,612 A | 8/1989 | Stocklin |
| 9,272,118 B1 | 3/2016 | Acton |

(Continued)

FOREIGN PATENT DOCUMENTS

EP 2224987 B1 6/2015

OTHER PUBLICATIONS

Riecke, et al. "4-Hz Transcranial Alternating Current Stimulation Phase Modulates Hearing", Brain Stimulation, vol. 8, No. 4, Jul. 1, 2015, pp. 777-783.

(Continued)

*Primary Examiner* — Mark W. Bockelman
(74) *Attorney, Agent, or Firm* — Carter, DeLuca & Farrell LLP

(57) ABSTRACT

A transcranial brain stimulation apparatus comprises an acoustic detection device for detecting acoustic signals as analog sound signals and an electrode arrangement including a plurality of electrodes which can be arranged in an operating configuration on a skull, wherein in the operating configuration during energization of the electrodes a current flow is generated through at least one auditory cortex of the cerebral cortex in the skull. A signal conversion device is configured to convert a respective analog sound signal into a first digital signal, and to determine a second digital signal from the first digital signal by extracting the envelope from the first digital signal and shifting the envelope by a predetermined amount of time greater than zero into the future or leaving it unshifted; and to convert the second digital signal into a current, and to energize the electrode arrangement in the operating configuration with this current.

15 Claims, 2 Drawing Sheets

(56) References Cited

U.S. PATENT DOCUMENTS 9,358,393 B1 6/2016 Lozano
9,452,286 B2 * 9/2016 Cowan ................. A61N 1/3756

OTHER PUBLICATIONS

Riecke, "Studying Effects of Transcranial Alternating Current Stimulation on Hearing and Auditory Scene Analysis", Advances in Experimental Medicine and Biology, Jan. 1, 2016, vol. 894, pp. 371-379.
International Search Report issued in corresponding PCT Application No. PCT/EP2017/073393 dated Dec. 12, 2017.

* cited by examiner

DEVICE FOR TRANSCRANIAL BRAIN STIMULATION

CROSS REFERENCE TO RELATED APPLICATIONS

This application is a national phase of PCT Application No. PCT/EP2017/073393 filed on Sep. 18, 2017, which claims the benefit of and priority to German Patent Application No. 10 2016 221 478.0, filed on Nov. 2, 2016, each of which are hereby incorporated by reference herein in their entirety.

TECHNICAL FIELD

The invention relates to an apparatus for transcranial brain stimulation, as well as a method and a device for calibrating this apparatus.

BACKGROUND

Non-invasive hearing aids which detect an acoustic signal through a microphone and subsequently reproduce the sound signal in the ear are known for improving the hearing ability of hearing-impaired persons. However, non-invasive hearing aids are not suitable for people having a severely impaired hearing ability.

For severely hearing-impaired people, invasive hearing aids are commonly used. In particular, cochlear implants are applied which electrically stimulate the acoustic nerve of the hearing-impaired persons. Implanted hearing aids indeed achieve good results, but require a surgical intervention.

In document EP 2 224 987 B1, an apparatus for suppressing tinnitus is described in which inter alia a brain stimulation is used to reduce the tinnitus of a patient.

The object of the invention is to provide an apparatus which improves the hearing ability of a hearing-impaired person by means of transcranial brain stimulation.

SUMMARY

This object is achieved by the apparatus according to claim 1. Further developments of the invention are defined in the dependent claims.

The apparatus according to the invention is used for transcranial brain stimulation and comprises an acoustic detecting device, such as a microphone, which detects acoustic signals as analog sound signals. Thus, the analog sound signals represent the sound pressures detected by the acoustic detection device. A respective analog sound signal represents in particular a given speech sequence, such as a sentence pronounced by a human being.

The apparatus further comprises an electrode arrangement of a plurality of electrodes which can be arranged on a skull of a human being or an animal in an operating configuration, wherein in the operating configuration during energization of the electrodes a current flow is generated through at least one auditory cortex of the cerebral cortex in the skull. Depending on the embodiment of the apparatus, only the auditory cortex in the left half of the skull or only the auditory cortex in the right half of the skull can be considered. In a preferred variant, however, both the auditory cortex in the left half of the skull and the auditory cortex in the right half of the skull are considered when arranging the electrodes. In this manner, the hearing ability of both ears of the corresponding human being or animal can be improved.

The apparatus according to the invention further comprises a signal conversion device. This device is configured to convert a respective analog sound signal into a first digital signal, the course of which corresponds to the respective analog sound signal. Here and in the following, the term course is to be understood as the time-dependent course. Furthermore, the above wording, according to which one signal corresponds in its course to another signal, is to be understood here and in the following such that both signals conform to each other except for a scaling factor.

The signal conversion device is further configured such that it determines in its operation a second digital signal from the first digital signal by extracting the envelope from the first digital signal and shifting the envelope by a predetermined amount of time greater than zero into the future or, where applicable, also leaving it unshifted. The shift into the future corresponds to a shift of the envelope along the time axis to a later point in time. In other words, this shift can be understood as a temporal delay of the envelope, and thus, of the converted current described below.

The term envelope is familiar to a skilled person, and corresponding methods for its extraction are known per se. The term envelope describes the temporal envelope that passes through local maxima of the absolute values of the corresponding signal for which the envelope is extracted. Normally, not all local maxima of the absolute values are considered, but the temporal envelope is determined in a predetermined frequency range of the signal. Here and in the following, the term envelope thus includes the temporal envelope and, where applicable, also the temporal envelope which was subjected to a correction. Such a correction can consist, for example, in setting the values of the (uncorrected) temporal envelope which exceed a predetermined percentage value (such as 25%) of the absolute maximum of the temporal envelope to the absolute maximum. This results in a distortion of the temporal envelope.

The signal conversion device of the apparatus according to the invention is further configured to convert the above-mentioned second digital signal into an electric current, the course of which corresponds to the second digital signal, and to energize the electrode arrangement in the operating configuration with this current.

The invention is based on the finding that a significant improvement of a person's hearing ability can be obtained by a transcranial brain stimulation which corresponds to the envelope of a corresponding sound signal. The application of the apparatus according to the invention does not require any surgical intervention, as is the case with invasive hearing aids. Only electrodes have to be attached to corresponding areas of the person's skull.

In a particularly preferred embodiment, the electrode arrangement comprises a pair of electrodes for the auditory cortex in the left half of the skull and/or a pair of electrodes for the auditory cortex in the right half of the skull. Thus, a maximum of two pairs of electrodes are used in the apparatus, so that the application of the apparatus is facilitated and its wearing comfort is improved.

In another preferred embodiment, the predetermined amount of time by which the envelope is shifted into the future is between 50 ms and 150 ms, and is preferably 100 ms. It has been shown experimentally that these values provide the best improvement of the hearing ability for most of the patients.

In another preferred embodiment, a Hilbert transformation of the first digital signal is performed during the extraction of the envelope. This Hilbert transformation is known per se and provides a complex number for each temporal signal value of the first digital signal. The temporal sequence of the absolute values of these complex numbers corresponds to the (unfiltered) envelope of the first digital signal.

In a further preferred embodiment, the signal conversion device is configured such that the extraction of the envelope comprises a bandpass filtering of the first digital signal subsequent to its Hilbert transformation in a predetermined frequency range. In particular, this frequency range is the band between 0 Hz and 10 Hz or a section of this band, such as the band between 4 Hz and 8 Hz. These frequency ranges reflect the frequency spectrum of individual syllables in speech signals very well.

In another preferred embodiment of the apparatus according to the invention, the signal conversion device comprises a signal processing unit and a stimulation unit. These are configured such that the signal processing unit receives the respective sound signal from the acoustic detection device and determines the second digital signal therefrom, wherein the second digital signal is firstly converted by the signal processing unit into an electric voltage, the course of which corresponds to the second digital signal and which is output to the stimulation unit. The stimulation unit converts this voltage into the electric current described above, which is used to energize the electrode arrangement.

In another preferred embodiment of the apparatus according to the invention, the current for energizing the electrode arrangement is defined such that its maximum value is between 0.5 mA and 2 mA, in particular at 2 mA or less and preferably at 1 mA. This ensures that the current is below the patient's threshold of perception.

In another preferred embodiment, the apparatus according to the invention is wearable (as a whole) by the human being or animal to whose skull the electrodes of the electrode arrangement are attached in the operating configuration. In particular, it can be attached (as a whole) to the skull of the human being or animal. In this manner, it is ensured that the device can be carried by the patient.

In another preferred embodiment, the apparatus according to invention further comprises an acoustic output device for outputting acoustic signals based on the analog sound signals in the region of one or both ears of the human being or animal to whose skull the electrodes of the electrode arrangement are attached in the operating configuration. This output preferably occurs directly after the detection of the acoustic signals by the acoustic detection device. With this additional acoustic output, the patient's hearing ability can be further improved. The acoustic signals output based on the analog sound signals substantially correspond to the originally detected acoustic signals, but can be subjected to a suitable post-processing for signal improvement. For example, signal noise can be removed or suppressed.

In addition to the above apparatus according to the invention, the invention also includes a method for calibrating the same. During this calibration method, in the presence of an acoustic signal, an electroencephalogram in the form of a temporal voltage curve is detected in the region of at least one auditory cortex of the cerebral cortex in the skull of a human being or animal, for which the apparatus according to the invention is to be used, by means of an electrode arrangement consisting of several electrodes. For this purpose, the electrodes of the electrode arrangement are attached to the skull at suitable positions. In particular, these positions may correspond to the above operational configuration. The electrode arrangement preferably consists of a pair of electrodes for the auditory cortex in the left half of the skull and/or a pair of electrodes for the auditory cortex in the right half of the skull. When applicable, the electrode arrangement may be the electrode arrangement of the apparatus to be calibrated.

With methods corresponding to those in the apparatus according to the invention, the (digital or digitized) envelope of the electroencephalogram is extracted and by means of cross correlation the time offset is determined which has the greatest correspondence between the envelope, which is extracted by the apparatus to be calibrated and which is based on the present acoustic signal and calculated in parallel with the detection of the electroencephalogram, and the envelope of the electroencephalogram. Thus, in a manner known per se, the maximum correlation value corresponding to the cross correlation of the two envelopes is determined. This time offset is then stored as a predetermined time amount in the apparatus to be calibrated, and is then used by the same. When performing the calibration, the apparatus for transcranial brain stimulation preferably only extracts the envelope without supplying electric current to the electrode arrangement of the device.

With the calibration method described above, a patient-specific adaptation of the apparatus to the time offset between the occurrence of acoustic signals and their processing in the brain is obtained. In this way, the apparatus according to the invention is optimally adjusted to the corresponding wearer.

In addition to the calibration method described above, the invention includes a calibration device configured to carry out this calibration method. In other words, this device comprises means for detecting an encephalogram, means for extracting the envelope of the encephalogram and for determining the time offset by cross-correlation, and means for transmitting the respective time offset to the apparatus to be calibrated.

The calibration device described above can be a component which is separated from the apparatus to be calibrated. Nevertheless, it is also possible that the calibration device is part of the apparatus for transcranial brain stimulation according to the invention.

BRIEF DESCRIPTION OF THE DRAWINGS

Exemplary embodiments of the invention are described in detail below with respect to the attached drawings, in which.

DETAILED DESCRIPTION

Figure 1:
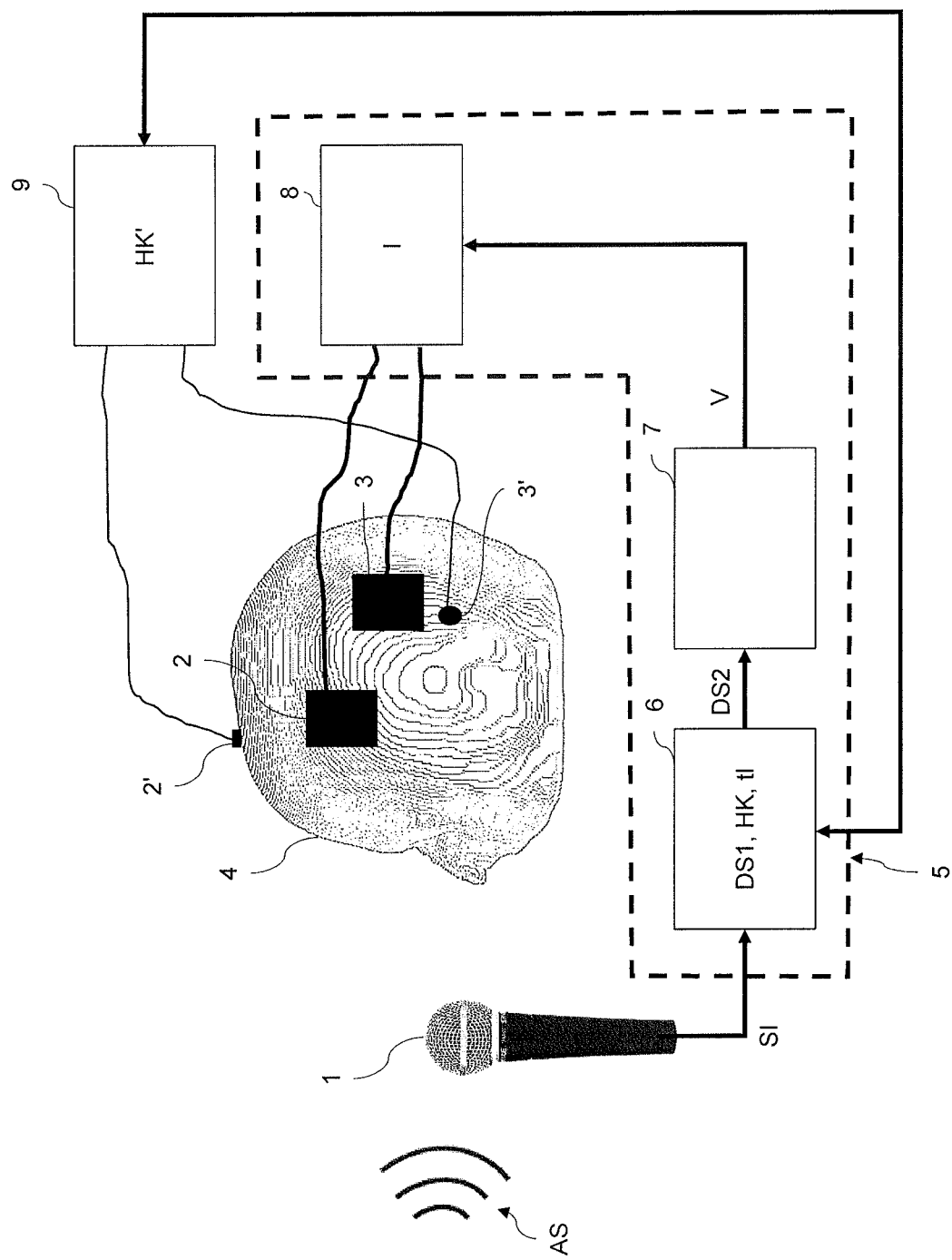
FIG. 1 is a schematic view of an embodiment of the apparatus for transcranial brain stimulation according to the invention.

FIG. 1 shows a schematic view of an embodiment of an apparatus for transcranial brain stimulation according to the invention. The apparatus is used to improve the hearing ability of a hearing-impaired person by suitably stimulating the cerebral cortex with an electric current. In this sense, the apparatus represents a hearing aid. The components of the apparatus described below are preferably configured such that they are wearable and can be carried by the hearing-impaired person.

The apparatus of FIG. 1 comprises a microphone 1, which is preferably implemented in miniaturized form and attached in the region of one or both ears of the hearing-impaired person. Via microphone 1, acoustic signals are detected which are denoted with AS in FIG. 1 and are indicated by three concentric circle segments. The acoustic signals detected by microphone 1 represent analog signals, which are denoted as sound signals SI in FIG. 1. A detected single sound signal SI preferably represents a contiguously spoken speech sequence which, for example, is pronounced by another person communicating with the hearing-impaired person. In particular, the speech sequence can be a spoken sentence. The sound signals SI are fed to a signal conversion device 5. The components of this device are preferably accommodated in a common housing, which may be attached, for example, to or behind the ear of the hearing-impaired person.

Two electrodes 2 and 3 are attached to the hearing-impaired person's skull, which is denoted by 4 in FIG. 1, above the left ear. The electrodes are positioned such that an electric current flowing between these electrodes, which is generated by the transcranial electrode stimulator 8 described further below, stimulates the auditory cortex in the left half of the skull. In the 10-20 EEG system, the auditory cortex of the left cerebral hemisphere is located approximately below electrode position T3, whereas the cortex of the right cerebral hemisphere is located approximately below electrode position T4. In order to obtain a current flow through the cortex of the left cerebral hemisphere, electrode 2 can be located at position F3 and electrode 3 can be located at position T5 in the 10-20 EEG system, for example. Electrodes 2 and 3 are connected to the electrode stimulator 8 via electric cables.

Preferably, also on the right half of the skull, two electrodes are positioned which allow current to flow through the right auditory cortex by means of the transcranial electrode stimulator 8. For example, one of these electrodes can be located at position F4 and the other at position T6 in the 10-20 EGG system. With usage of electrodes on both halves of the skull, the hearing ability of both ears of the hearing-impaired person is improved. If there is hearing impairment for only one ear, only one pair of electrodes is used for the auditory cortex of the impaired ear. In the following, the device is described only with respect to the stimulation of electrodes 2 and 3, wherein the stimulation of the electrodes on the other half of the skull is executed analogously.

The sound signal SI detected by microphone 1 is fed to a signal processor 6 within the sound conversion device 5. For example, the signal processor 6 and the digital-to-analog converter 7 described below can be implemented in a common integrated circuit. The SI signal is pre-amplified in the signal processor and then digitized, thus obtaining a first digital signal DS1. Using signal processor 6, the envelope HK (i.e. the temporal envelope) is determined from the first digital signal DS1 in a manner known per se. In the embodiment described here, the envelope is extracted in a predetermined frequency range of the first digital signal DS1, so that high-frequency oscillations in the sound signal are no longer contained in the envelope. In detail, during the envelope extraction, the Hilbert transformation known per se is applied to the digital signal DS1, which transformation provides complex values whose absolute values represent the unfiltered envelope. This curve is then subjected to low-pass filtering in the frequency range between 0 Hz and 10 Hz, which corresponds to the frequency range of individual syllables relevant for hearing. In the embodiment described here, the filtered curve represents the envelope HK.

Figure 2:
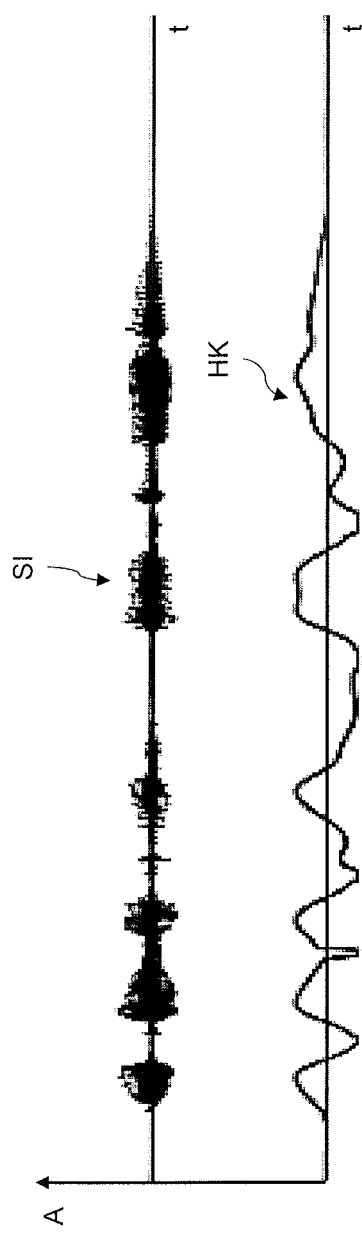
FIG. 2 is a schematic view of a sound signal detected by the apparatus of FIG. 1 and the envelope extracted therefrom.

FIG. 2 shows a diagram depicting an example of the extraction of an envelope by means of the apparatus of FIG. 1. The time t is displayed along the abscissa of the diagram and the amplitude A is displayed along the coordinate. The detected analog sound signal SI is shown in the upper part of the diagram. From this signal, the envelope HK is obtained, which is shown in the lower part of the diagram. The envelope is a zero-mean curve, i.e. the values of the envelope reflect the deviation from the signal mean value.

In a next step in the signal processing unit 6, the envelope HK is shifted into the future by a predetermined amount of time $t1$. The amount of time reflects the offset between the occurrence of the acoustic signal AS and the time of signal processing in the brain. The value of the amount of time can be suitably determined in advance by experiments and can be set to 100 ms, for example. In a particularly preferred embodiment, this amount of time is determined during a calibration method of the apparatus described here, wherein this calibration method is explained in more detail below.

The envelope shifted by the amount of time $t1$ represents a second digital signal DS2, which is subsequently fed to the digital-to-analog converter 7 within the signal conversion device 5. This digital-to-analog converter provides an electric voltage V, the time course of which corresponds to the second digital signal DS2. The voltage V is finally fed to the transcranial electrode stimulator 8, which converts the voltage into an electric current whose temporal course corresponds to the voltage V. The stimulator 8 supplies this current to electrodes 2 and 3. The stimulator ensures that the desired current flows through the auditory cortex between electrodes 2 and 3 also in case of a change of the impedance on the skull. With the electrode stimulation according to the envelope of the sound signal, a significant improvement in hearing ability can be achieved, especially when the original acoustic signal contains a high noise level.

In order to adapt the time $t1$ described above specifically to the hearing-impaired person, in a preferred embodiment, a calibration of the apparatus of the invention is carried out using the schematically indicated calibration device 9. Two electrodes 2' and 3' are connected to this calibration device, which, similar to electrodes 2 and 3, are arranged on the skull 4 such that they bridge the auditory cortex at the left ear.

During the calibration operation, a predetermined acoustic signal is generated. This signal is processed as described above by the signal conversion device 5, but without generating the current I by the electrode stimulator 8. At the same time, for the incoming acoustic signal, the electroencephalogram, i.e. the voltage pulses occurring between electrodes 2' and 3', is determined by the calibration device 9. In analogy to the extraction of the envelope HK described above, the device 9 extracts the envelope HK' of the voltage signals from this electroencephalogram.

The calibration device 9 is able to communicate via a suitable interface with the signal processor 6 of the device to be calibrated, as indicated by a double arrow in FIG. 1. The device reads the extracted envelope HK via this interface and determines by means of cross correlation the time offset having the greatest correspondence between the envelope HK and the envelope HK'. Thus, the time offset having the maximum value of the cross correlation function of the two envelopes is determined. This time offset reflects the person-specific time shift between the incoming acoustic signal and its processing in the brain. The determined time offset is then transmitted by the device 9 via the above described interface to the signal processor 6, which stores this time offset as the predetermined time amount $t1$ and uses the same in operation for shifting the envelope. In this sense, the transmitted time offset represents a calibrated value for the apparatus for transcranial brain stimulation.

The above described calibration device was described as a separate component that is not part of the apparatus for transcranial brain stimulation. However, it is also possible for the corresponding calibration function to be integrated in the apparatus for transcranial brain stimulation.

The above described embodiments of the invention have a number of advantages. In particular, a simple non-invasive hearing aid is created that improves the hearing ability of hearing-impaired persons by stimulating the auditory cortex in the brain. In contrast to cochlear implants, this hearing aid does not require a surgical intervention, but can be easily put into operation by attaching electrodes to the skull. With the hearing aid according to the invention, in particular an improvement of the hearing ability is achieved for speech signals which are embedded in a strong background noise.

The invention claimed is:

1. An apparatus for transcranial brain stimulation comprising:
   an acoustic detection device for detecting acoustic signals as analog sound signals;
   an electrode arrangement comprising a plurality of electrodes which can be arranged in an operating configuration on a skull of a human being or animal, wherein in the operating configuration during energization of the electrodes a current flow is generated through at least one auditory cortex of a cerebral cortex in the skull; and
   a signal conversion device configured to:
   i) convert a respective analog sound signal into a first digital signal, the course of which corresponds to the respective analog sound signal, and to determine a second digital signal from the first digital signal by extracting an envelope from the first digital signal and shifting the envelope by a predetermined amount of time greater than zero into the future or leaving it unshifted; and
   ii) convert the second digital signal into a current, the course of which corresponds to the second digital signal, and to energize the electrode arrangement in the operating configuration with this current.

2. The apparatus according to claim 1, wherein the electrode arrangement consists of a pair of electrodes for the auditory cortex in a left half of the skull and/or a pair of electrodes for the auditory cortex in a right half of the skull.

3. The apparatus according to claim 1, wherein the predetermined amount of time is between 50 ms and 150 ms.

4. The apparatus according to claim 1, wherein the signal conversion device is configured such that a Hilbert transformation of the first digital signal is carried out during extraction of the envelope.

5. The apparatus according to claim 4, wherein the signal conversion device is configured such that the extraction of the envelope comprises a bandpass filtering of the first digital signal subsequent to its Hilbert transformation in a predetermined frequency range, the predetermined frequency range being the band between 0 and 10 Hz or a section thereof.

6. The apparatus according to claim 1, wherein the signal conversion device comprises a signal processing unit and a stimulation unit which are configured such that the signal processing unit receives the respective analog sound signal from the acoustic detection device and determines the second digital signal therefrom, wherein the second digital signal is firstly converted by the signal processing unit into a voltage, the course of which corresponds to the second digital signal and which is output to the stimulation unit which converts the voltage into the current for energizing the electrode arrangement.

7. The apparatus according to claim 1, wherein the current is set such that its maximum value is between 0.5 mA and 5 mA.

8. The apparatus according to claim 1, wherein the apparatus is wearable by the human being or animal to whose skull the electrodes or the electrode arrangement are attached in the operational configuration, and is attachable to the skull of the human being or animal.

9. The apparatus according to claim 1, further comprising an acoustic output device for outputting acoustic signals based on the analog sound signals in the region of one ear or both ears of the human being or animal to whose skull the electrodes or the electrode arrangement are attached in the operating configuration.

10. A method for calibrating an apparatus according to claim 1, wherein
   in the presence of an acoustic signal, an electroencephalogram in the form of a temporal voltage curve is detected in a region of at least one auditory cortex of the cerebral cortex in the skull of a human or animal, for which the apparatus for transcranial brain stimulation is to be used, by an electrode arrangement comprising a plurality of electrodes;
   an envelope of the electroencephalogram is extracted and a time offset having a greatest correspondence between the envelope which is extracted by the apparatus for transcranial brain stimulation and which is based on the present acoustic signal, and the envelope of the electroencephalogram is determined by cross correlation;
   the time offset is stored as a predetermined time amount in the apparatus for transcranial brain stimulation.

11. A device for calibrating an apparatus, wherein the device is configured to perform the method according to claim 10.

12. An apparatus for transcranial brain stimulation, comprising the device for calibrating an apparatus according to claim 11.

13. The apparatus according to claim 1, wherein the predetermined amount of time is 100 ms.

14. The apparatus according to claim 1, wherein the current is set such that its maximum value is at 2 mA or less.

15. The apparatus according to claim 1, wherein the current is set such that its maximum value is 1 mA.

* * * * *